United States Patent [19]

LeVahn et al.

[11] Patent Number: 4,718,151

[45] Date of Patent: Jan. 12, 1988

[54] RETRACTOR APPARATUS

[75] Inventors: Bruce A. LeVahn, New Brighton; Robert E. Olson, Roseville, both of Minn.

[73] Assignee: Minnesota Scientific, Inc., Minneapolis, Minn.

[21] Appl. No.: 869,347

[22] Filed: Jun. 2, 1986

Related U.S. Application Data

[62] Division of Ser. No. 669,362, Nov. 8, 1984, Pat. No. 4,617,916.

[51] Int. Cl.$^4$ ............................................. A44B 21/00
[52] U.S. Cl. ........................................ 24/535; 24/542; 248/DIG. 4; 128/20
[58] Field of Search ................. 24/530, 535, 542, 456, 24/236 R; 285/184; 128/20; 248/DIG. 4, DIG. 12

[56] References Cited

U.S. PATENT DOCUMENTS

| | | | |
|---|---|---|---|
| 497,064 | 5/1893 | Van Meter | 128/20 |
| 1,049,642 | 1/1913 | Baesel | 24/136 R |
| 1,059,948 | 4/1913 | Neberle | 248/DIG. 4 |
| 1,168,574 | 1/1916 | Spurr . | |
| 1,198,186 | 9/1916 | Brown | 248/DIG. 4 |
| 1,230,873 | 6/1917 | Crossley . | |
| 1,382,783 | 6/1921 | Howard | 128/20 |
| 1,460,697 | 7/1923 | Bendlin | 128/20 |
| 1,707,689 | 4/1929 | Sloan | 128/20 |
| 1,747,799 | 2/1930 | Straus | 128/20 |
| 2,066,699 | 1/1937 | Skelton | 248/279 |
| 2,177,921 | 10/1939 | Zofrey | 248/DIG. 4 |
| 2,469,904 | 5/1949 | Szuba | 248/DIG. 4 |
| 2,557,430 | 5/1950 | Hensley | 248/102 |
| 2,586,488 | 2/1952 | Smith | 128/20 |
| 2,594,086 | 4/1952 | Smith | 128/20 |
| 2,623,517 | 12/1952 | Barlow | 128/20 |
| 2,670,731 | 3/1954 | Zoll et al. | 128/20 |
| 2,670,732 | 3/1954 | Nelson | 128/20 |
| 3,038,468 | 6/1962 | Raeuchle | 128/20 |
| 3,040,739 | 6/1962 | Grieshaber | 128/20 |
| 3,221,743 | 12/1965 | Thompson et al. | 128/303 |
| 3,522,799 | 8/1970 | Gauthier | 128/20 |
| 3,572,326 | 3/1971 | Jensen | 128/20 |
| 3,638,973 | 2/1972 | Poletti | 285/184 |
| 3,749,088 | 7/1973 | Kohlmann | 128/20 |
| 3,810,462 | 5/1974 | Szpur | 128/20 |
| 3,858,578 | 1/1975 | Milo | 128/20 |
| 3,910,538 | 10/1975 | Baitella | 248/122 |

(List continued on next page.)

FOREIGN PATENT DOCUMENTS

1235185  5/1960  France .
 446439  3/1949  Italy .

OTHER PUBLICATIONS

"Pilling Retractor Systems," four-page brochure of Narco Scientific, Pilling Division, Fort Washington, Pa., dated 12/81.
"Thompson Retractor," two-page brochure of Richard C. Thompson, M.D., San Mateo, Calif.
Thompson, R. C. et al, "Mechanical Aids at the Operating Table," *California Medicine*, vol. 97, No. 1, pp. 28–30, Jul. 1962.
Price List of Automatic Retractor Holder of Great Eastern Lumber Co., one page.

*Primary Examiner*—Victor N. Sakran
*Attorney, Agent, or Firm*—Kinney & Lange

[57] ABSTRACT

A retractor apparatus for attachment to a rail of a surgical table includes first, second and third support rods and first, second and third clamps. The first support rod is attached to the rail of the surgical table and permits movement about and along a vertical axis of the first rod. The second rod is attached to an upper section of the first rod with the second clamp. The second clamp permits movement of the second support rod about an axis of the first rod and about an axis of the second support rod and permits pivotal movement of the second rod with respect to the first rod about a pivotal axis of the second clamp. The third clamp clamps the third rod to the second rod and permits movement of the third rod along and about the axis of the second rod and about the axis of the third rod and permits movement about a pivotal axis of the third clamp. The third rod includes first and second spaced apart leg portions that extend over the surgical table on opposite sides proximate the incision for support of retractors.

6 Claims, 7 Drawing Figures

U.S. PATENT DOCUMENTS

| | | | |
|---|---|---|---|
| 3,965,890 | 6/1976 | Gauthier | 128/20 |
| 4,010,741 | 3/1977 | Gauthier | 128/20 |
| 4,099,521 | 7/1978 | Nestor et al. | 128/20 |
| 4,143,652 | 3/1979 | Meier et al. | 128/20 |
| 4,254,763 | 3/1981 | McCready et al. | 128/20 |
| 4,337,762 | 7/1982 | Gauthier | 128/20 |
| 4,355,631 | 10/1982 | LeVahn | 128/20 |
| 4,402,481 | 9/1983 | Sasaki | 248/DIG. 4 |
| 4,421,108 | 12/1983 | Cabrera et al. | 128/20 |

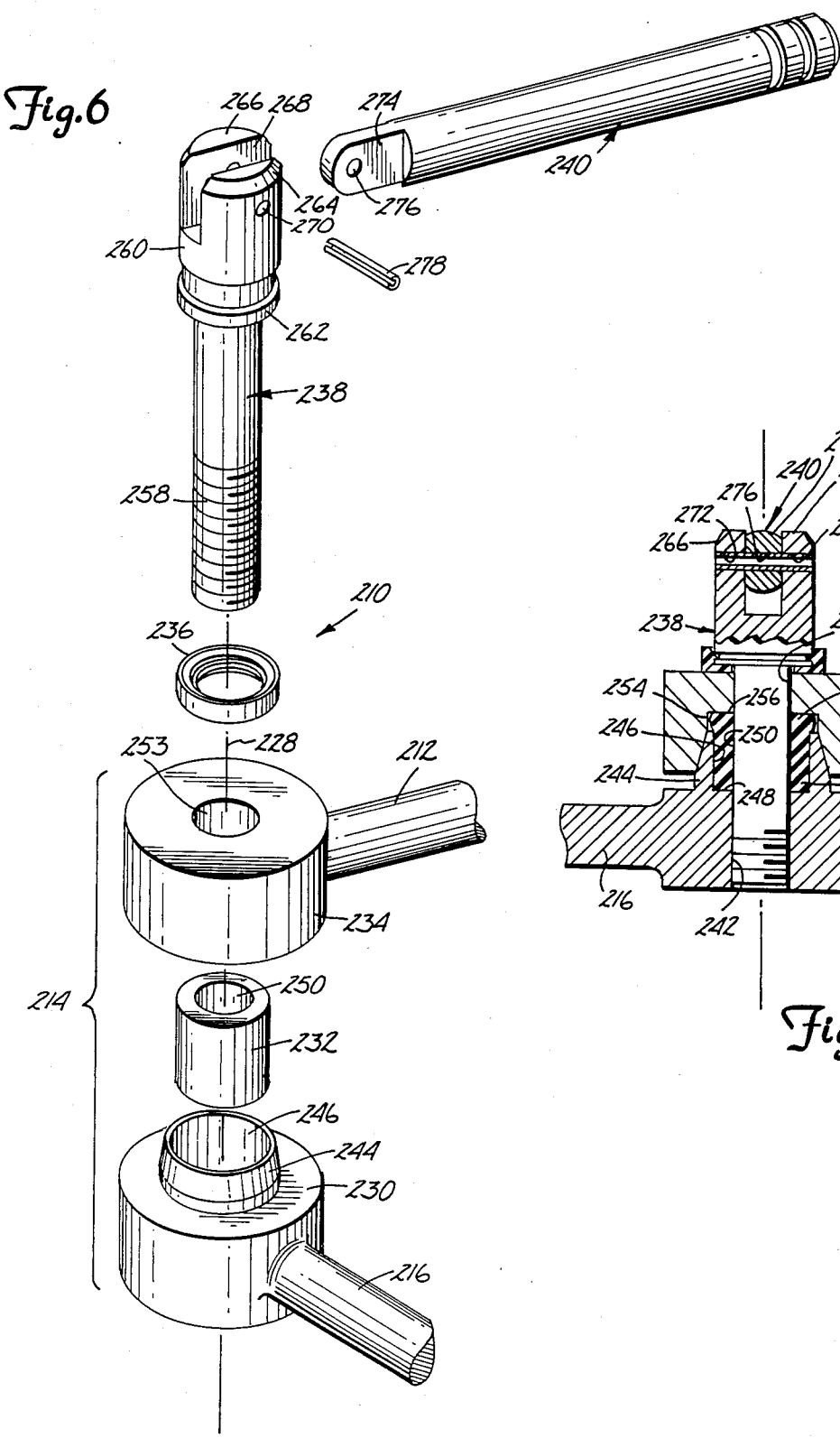

RETRACTOR APPARATUS

This is a division of application Ser. No. 06/669,362, filed Nov. 8, 1984, now U.S. Pat. No. 4,617,916.

BACKGROUND OF THE INVENTION

1. Field of the Invention

The present invention relates to surgical retractor apparatus, and in particular, it relates to a retractor apparatus that is attached directly to an operating table rail for use in surgery.

2. Description of the Prior Art

In abdominal and chest surgery, it is customary to use a retractor apparatus that is directly mounted to the operating table. The apparatus includes retractors that hold back tissue proximate to the surgical incision to enable the surgeon to work in areas such as the abdominal area or chest cavity.

Most retractor apparatus are positioned above a surgical drape that defines the sterile area where the surgeon and other attendants need to move to perform the surgery correctly and efficiently. The usefulness of any retractor apparatus is limited by the number of ways that the retractors can be positioned with respect to the incision of the body and with the ease and simplicity that the surgeon can adjust the relative position of the retractor before and during surgery. In addition, the retractor apparatus should not pose any great obstructions to the surgeon's movement during surgery or take up a great amount of space, limiting the movement of the surgeon and other attendants.

There have been many attempts in developing a suitable retractor apparatus. For example, the following patents illustrate retractors and/or retractor support apparatus that are movable along a single plane:

| Inventor | U.S. Pat. No. |
| --- | --- |
| Sloan | 1,707,689 |
| Smith | 2,586,488 |
| Smith | 2,594,086 |
| Cooper | 2,893,378 |
| Raeuchle | 3,038,468 |
| Kohlman | 3,749,088 |
| Gauthier | 3,965,890 |
| Trumbull et al | 3,998,217 |
| Gauthier | 4,010,741 |
| Hursom | 4,048,987 |
| Gauthier | 4,337,762 |
| Estes et al | 4,421,107 |
| Cabrera | 4,421,108 |
| Country | Patent No. |
| Italy | 446,439 |

In addition, there are several patents and one brochure that illustrate devices and apparatus that permit pivotal movement of the retractor and/or some component of the apparatus about one axis with some also including movement along one plane:

| Inventor | U.S. Pat. No. |
| --- | --- |
| Van Meter | 497,064 |
| Spurr | 1,168,574 |
| Crossley | 1,230,873 |
| Barlow et al | 2,623,517 |
| Nelson | 2,670,732 |
| Grieshaber | 3,040,739 |
| Jensen | 3,572,326 |
| LeVahn | 4,355,631 |
| Country | Patent No. |
| Italy | 446,439 |
| Germany | 460,145 |

BROCHURES

"Pilling Retractor Systems", four-page brochure of Narco Scientific, Pilling Division, Fort Washington, Pa. dated 12/81.

There are also several patents, brochures and articles that either illustrate or discuss retractor apparatus that permit pivotal movement about two axes with some also permitting movement along a single plane:

| Inventor | U.S. Pat. No. |
| --- | --- |
| Nelson | 267,599 |
| Straus | 1,747,799 |
| Skelton | 2,066,699 |
| Zoll et al | 2,670,731 |
| Thompson et al | 3,221,743 |
| Szpur | 3,810,462 |
| McGuire | 3,823,709 |
| Baitella | 3,910,538 |
| Meier et al | 4,143,652 |
| McCready et al | 4,254,763 |
| Country | Patent No. |
| France | 1,235,185 |

BROCHURES

"Thompson Retractor," two-page brochure of Richard C. Thompson, M.D., San Mateo, Calif.

Price List of Automatic Retractor Holder of Great Eastern Lumber Company, Inc., N.Y., N.Y.

"Bookwalter Retractor," two-page brochure of Codman & Shurtleff, Inc., Randolph, Mass.

ARTICLES

King, W. B., "Use of Table-Fixed Abdominal Retractors," *American Journal of Surgery*, Vol. 108, pp. 606–609, Nov. 1964.

Thompson, R. C. et al, "Mechanical Aids at the Operating Table," *California Medicine*, Vol. 97, No. 1 pp. 28–30, July 1962.

At least two prior art patents, the Milo U.S. Pat. No. 3,858,578 and the Poletti U.S. Pat. No. 3,638,973 disclose retractor arms that are movable through the use of ball joints. Although ball joints provide a great degree of flexibility and movement, holding power and rigidity are sacrificed.

In many of the above prior art references, the surgeon does not have the ability to position the retractor universally, but is limited by the limited movement of retractor support apparatus. In addition, some of the developments in retractor apparatus in attempting to improve versatility in movement have sacrificed space and created obstructions for the surgeon.

SUMMARY OF THE INVENTION

The present invention provides a retractor apparatus that allows the surgeon to quickly position and adjust retractors along at least three axes of rotation. The retractor support apparatus includes first, second and third rigid support rods and first, second and third clamping mechanisms. The first clamping mechanism connects a lower section of the first support rod to the rail of the operating table. The second rod is connected to an upper section of the first rod by the second clamping mechanism. The second clamping mechanism permits pivotal movement of the second rod about the first rod and movement of the second rod about its own axis and movement of the second rod about an axis of the clamping mechanism. The third rod includes spaced-apart leg portions extending on opposite sides of the incision. Retractors are supported from the third rod. The third rod is connected to the other end of the second rod by the third clamping mechanism. The third clamping mechanism permits the third rod to be pivoted about the axis of the second rod and pivoted about its own axis and pivoted with respect to the second rod about the pivotal axis of the third clamping mechanism.

The retractor apparatus of the present invention permits the surgeon, or one of his attendants, to adjust the relative position of the retractors by simply operating any one of the clamping mechanisms, alone or in combination, with a minimum of effort. The apparatus provides movable joints through the clamping mechanisms while also providing a joint that is exceptionally rigid, just as rigid as the support rods. The support apparatus does not require much space and provides little obstruction to the surgeon and attendants.

BRIEF DESCRIPTION OF THE DRAWINGS

FIG. 6 is an exploded perspective view of a clamping mechanism of an auxiliary retractor support device of the present invention.

FIG. 7 is a sectional view of the clamping mechanism of the auxiliary retractor support device of FIG. 6 with portions shown whole.

DETAILED DESCRIPTION OF THE PREFERRED EMBODIMENTS

Figure 1:
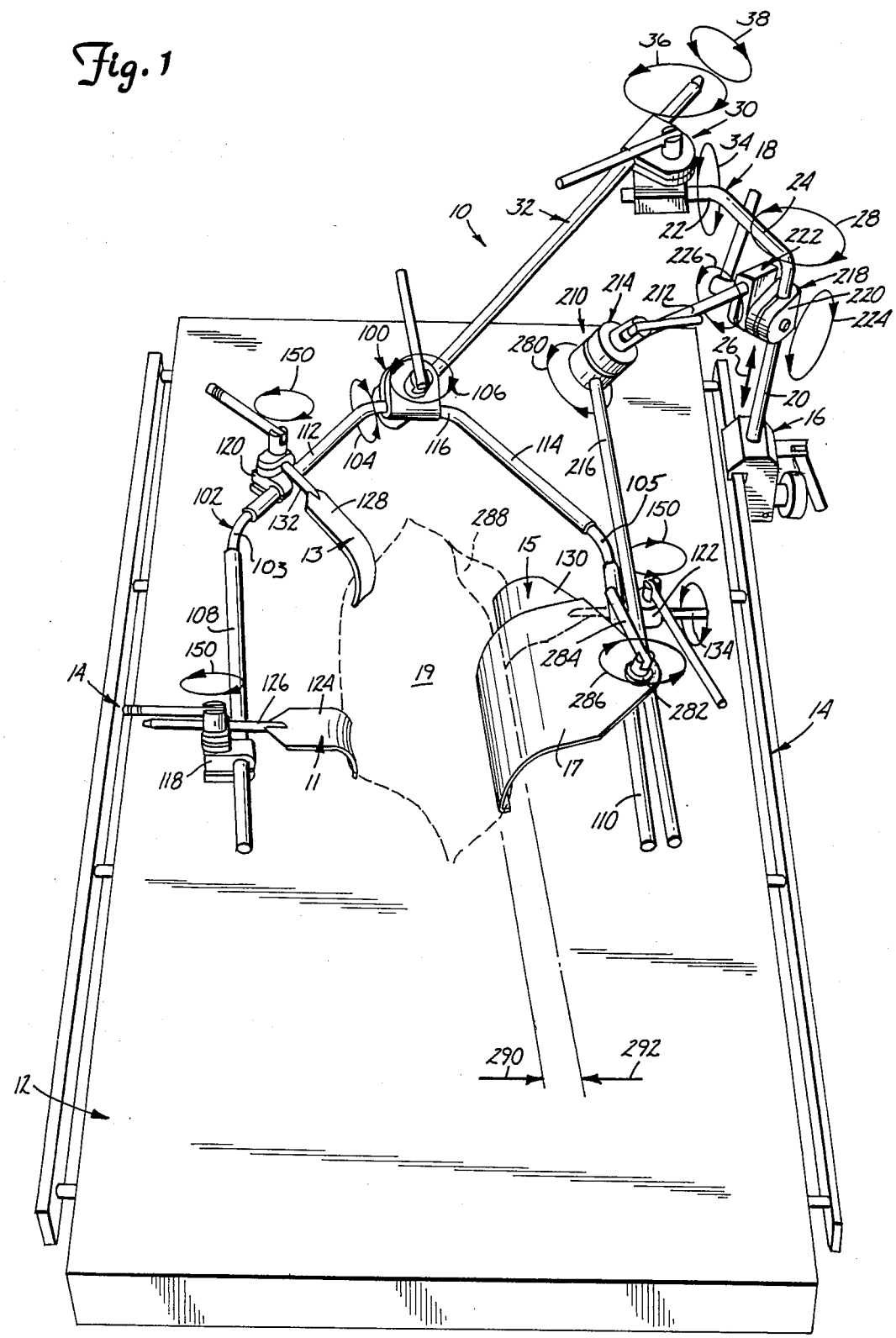
FIG. 1 is a perspective view of the retractor support apparatus of the present invention.

A retractor support apparatus of the present invention is generally indicated at 10 in FIG. 1. The retractor support apparatus 10 is used to support one or more retractors 11, 13, 15 and 17 above an operating table 12. The operating table 12 has side rails 14 to which retractor supports are commonly attached. The retractors are employed during major surgery, particularly of the chest or abdomen, and are applied to tissue proximate an area 19 of a surgical incision to hold back the cut tissue. Holding back the cut tissue exposes the area 19 in which the surgeon must work. The retractor support apparatus of the present invention provides a novel support that is movable about at least three axes so that a surgeon can adjust the position of the retractors in a quick and efficient manner before or during surgery.

The support apparatus 10 includes a side rail clamping device 16 that clamps onto a side rail 14 of the operating table 12. The side rail clamping device 16 is described in U.S. Pat. No. 4,355,631 issued to the inventor as the present application and assigned to the same assignee of the present invention and is hereby incorporated by reference. The clamp 16 is used to connect primary support rod 18 to the railing 14. The support rod 18 has a lower substantially vertical section 20 and an upper substantially horizontal section 22 and preferably a midsection 24 disposed angularly with and connecting the lower and upper sections with each other. The lower section 20 insertably engages the clamp 16 so that when the clamp 16 is loosened, the support post 18 is movable in a substantially vertical direction as indicated by arrow 26 and is fixedly retained with respect to rotation about the axis of the lower section 20.

A pivotal clamp 30 pivotally connects the upper section 22 of the support 18 with an extension rod 32. The extension rod 32 is retained in position in a rigid and fixed fashion, and when the clamp is released, the rod 32 is movable about three separate axes or has three degrees of freedom. First, the clamp 30 is rotatably movable about the axis of the upper section 22 of the support member 18, as indicated by arrows 34. Second, the clamp permits pivotal movement of the extension rod 32 about a pivotal axis running through the clamp as indicated by arrows 36. Third, the extension rod is rotatable about its own axis, as indicated by arrows 38. In addition, the rod 32 is movable along the axis of the upper section 22 and is movable along its own axis.

Figure 2:
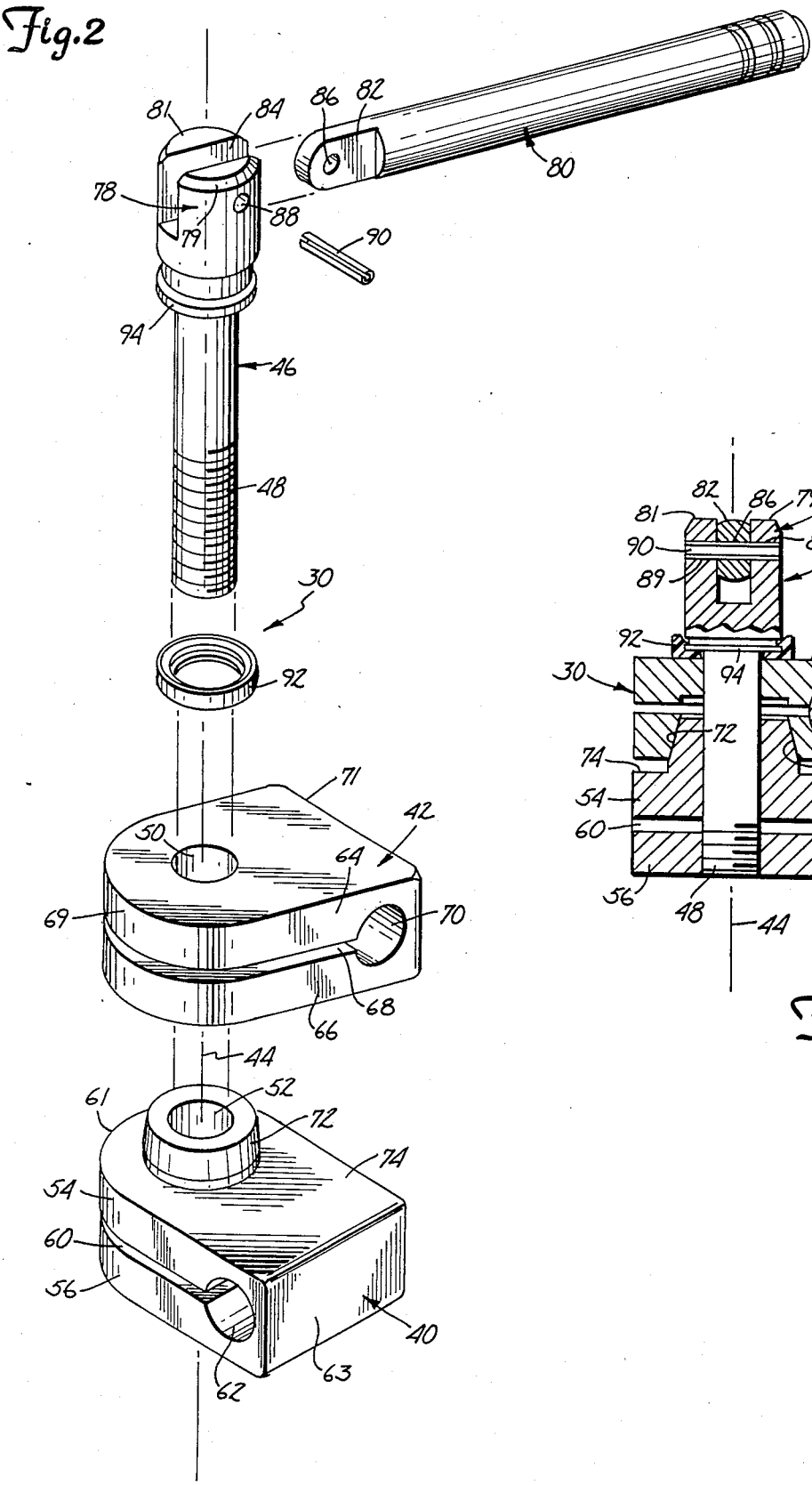
FIG. 2 is an exploded perspective view of one clamping mechanism of the present invention.
Figure 3:
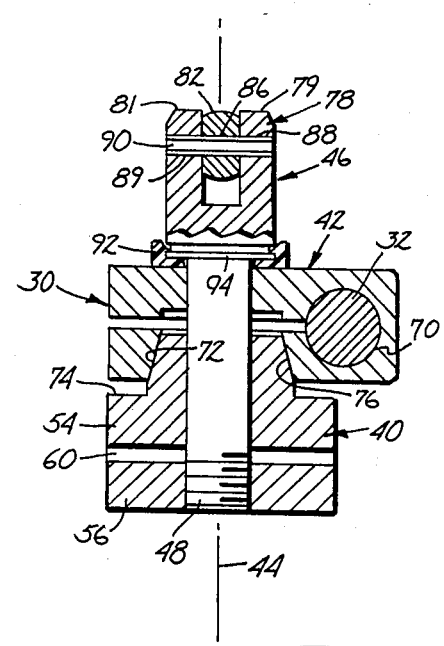
FIG. 3 is a sectional view of the clamping mechanism of FIG. 2 with portions shown whole.

The clamp 30 is more fully illustrated in FIGS. 2 and 3. The clamp 30 includes a lower clamping section 40 and an upper clamping section 42 in a pivotal relationship about a pivot axis 44. A retaining bolt 46, having a lower threaded section 48, extends through a bore 50 of the upper clamping section 42 and into a threaded bore 52 in the lower clamping section 40.

The lower clamping section 40 is of a unitary construction, preferably machined from a single block of stainless steel, and has an upper and a lower leg 54 and 56 separated by a slot 60. The slot 60 extends from one end 61 of the clamping section 40 to a clamping bore 62 located proximate an opposite end 63. The clamping bore 62 receives and clamps a rod section, such as section 22, described with reference to FIG. 1. The legs 54 and 56 are resiliently movable with respect to each other such that the clamping bore 62 is reduced sufficiently in size to frictionally clamp the rod section.

Similarly, the upper clamping section 42 is of a unitary construction, preferably machined from a single piece of stainless steel, and includes an upper leg 64 and a lower leg 66, separated by a slot 68. The slot 68 extends from one end 69 of the clamping section to a clamping aperture 70 proximate an opposite end 71. The legs 64 and 66 are resiliently movable with respect to each other such that the clamping bore 62 is reduced sufficiently in size to clamp a rod, such as rod 32, as described with reference to FIG. 1.

The lower clamping section 40 has an upwardly-extending frusto-conical portion 72 on an upper surface 74 thereof for frictional engagement with a frusto-conical recess 76 disposed in the lower leg 66 of the upper clamping section 42. The aperture 52 is disposed substantially coaxially within the frusto-conical portion 72. The aperture 50 communicates with and is disposed substantially coaxially with respect to the frusto-conical recess 76. The frusto-conical portion 72 insertably engages the frusto-conical recess 76 so that the clamping section 40 and the clamping section 42 pivot about the axis 44 with the apertures 50 and 52 in substantial alignment.

The bolt 46 has a head portion 78 opposite from the threaded section 48. The head portion 78 has first and second upwardly extending retaining members 79 and 81 respectively, separated by a slot 84. The retaining members 79 and 81 have substantially aligned apertures 88 and 89, respectively. A handle 80 has a slot-engaging portion 82 that movably engages the slot 84 of the head portion 78. The slot-engaging portion 82 of the handle 80 has an aperture 86 extending therethrough that is alignable with an apertures 88 and 89. A spring pin 90 insertably engages the apertures 88, 86 and 89 to pivotally attach the handle 80 to the head portion 78. The handle 80 is pivotal about the pin 90 from one side of the bolt to another side of the bolt 46, approximately 180° to facilitate turning of the bolt 46.

A friction-reduction ring 92 is disposed between the upper clamping section 42 and the head portion 78 of the pin 46. The ring engages an annular flange 94 of the head portion 78 defining the lowermost section of the head portion 78. The ring 92 is made of a material that reduces friction between the flange 94 and the clamping section 42. One suitable material is sold under the trademark "DELRIN" by DuPont De Nemours & Co. of Wilmington, Del.

To operate the clamp 30, rods are inserted into the clamping bores 62 and 70 of the clamping sections 40 and 42, respectively, such as rod 32 and rod section 22, as illustrated in FIG. 1. The rod 32 and rod section 22 are pivotally moved about the axis 44 by pivoting the clamping sections 40 and 42 with respect to each other. The rod 32 is moved in a selected position within the bore 70 and the bore 62 is moved in a selected position on the rod section 22. The bolt 46 is then turned, preferably clockwise, moving the legs 54 and 56 toward each other, thereby frictionally retaining the rod in the bore 62, and moving the legs 64 and 66 toward each other frictionally retaining the rod in the bore 70, and frictionally binding the frusto-conical section 72 with the frusto-conical recess 76 such that the clamping sections 40 and 42 are restricted from movement with respect to each other. The frusto-conical section and frusto-conical recess provide a large area of metal to metal contact to securely retain the clamping section in a clamping position. The ring 92, being made of a low friction material, helps to turn the bolt 46 more tightly and therefore increasing the clamping force of the clamping sections 40 and 42.

To loosen the clamp 30, the handle 80 is simply turned in an opposite direction, almost immediately releasing the clamping sections 40 and 42 from frictional engagement and permitting the legs 54 and 56 and legs 64 and 66 to move away from each other releasing the rods within the bores 62 and 70, all respectively. It will be appreciated that by simply turning the bolt 46 the rod 32 and anything attached to the rod 32 is quickly and easily positioned about three axes and retained in position and is quickly and easily released from position for further movement.

A second pivotal clamp 100 connects a retractor support rod 102 with the extension rod 32. The clamp 100 has the same structure as the clamp 30, described above with reference to FIG. 2. The clamp 100 permits pivoting of the retractor support rod 102 about the axis of the extension rod 32 as indicated by arrows 38, and about an axis of a midsection 116 of the retractor support rod 102 and about a pivotal axis of the clamp as indicated by arrows 106.

The retractor support rod 102 has preferably two spaced apart legs 108 and 110 which have angularly disposed sections 112 and 114, respectively, that are angularly disposed towards each other and connected by the midsection 116. The legs 108 and 110 are spaced sufficiently apart so that the legs are arranged on either side of the area 19 with sufficient room to position the retractors 11, 13, and 15.

It will be appreciated that the retractor support rod 102 is quickly positionable by operating either clamp 16, 30 or 100 or any combination of the three. The retractor support rod 102 can be raised vertically and moved horizontally as indicated by arrow 28 by operation of clamp 16. The support rod 102 can be inclined, with respect to the horizontal, toward one end or the other end of the operating table by operation of clamp 30 or 100 or both. In addition, operation of clamps 30 and 100 permit the support rod 102 to be tilted towards the left or the right side of the operating table. The retractor support rod 102 is also movable along the longitudinal axis of the operating table by adjusting the position of the extension rod 32 and the support post 18 and operation of clamps 16, 30 and 100.

The retractors 11, 13 and 15 are pivotally attached to the retractor support by retractor clamps 118, 120 and 122. The retractor clamps provide three degrees of freedom in positioning each of the retractors. The retractor 11 includes a retractor blade 124 and a retractor handle 126 attached to the blade and insertably engaging the clamp 118. Similarly, the retractors 13 and 15 have blades 128 and 130, and handles 132 and 134, which are inserted into clamps 120,122, all respectively.

The support rod 102 has corner portions 103 and 105 of reduced diameter, that is, a diameter smaller than that of sections 108, 112, 114 and 110. The corner portions 103 and 105 have a diameter sufficiently smaller than the adjacent sections 108 and 112 and adjacent sections 110 and 114 so that the retractor clamps are movable between sections 108 and 112, and 110 and 114 by only slightly loosening the clamp so that it is movable along the rod sections 108, 112, 114 and 110. The reduced diameter of the corner portions permits movement of slightly loosened clamps between rod sections.

Figure 4:
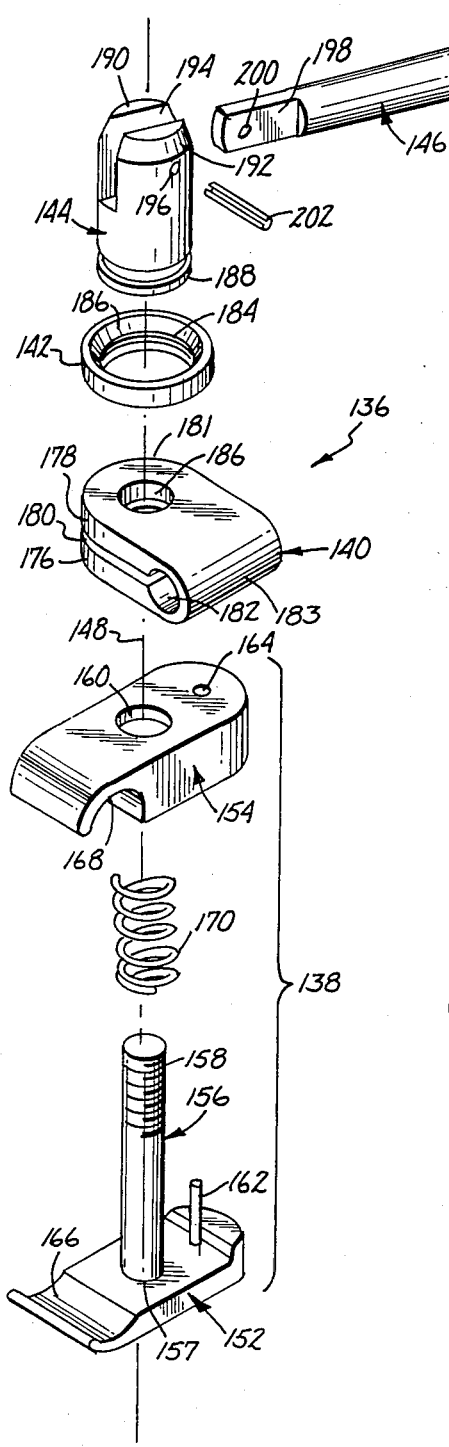
FIG. 4 is an exploded perspective view of a retractor clamping mechanism of the present invention.
Figure 5:
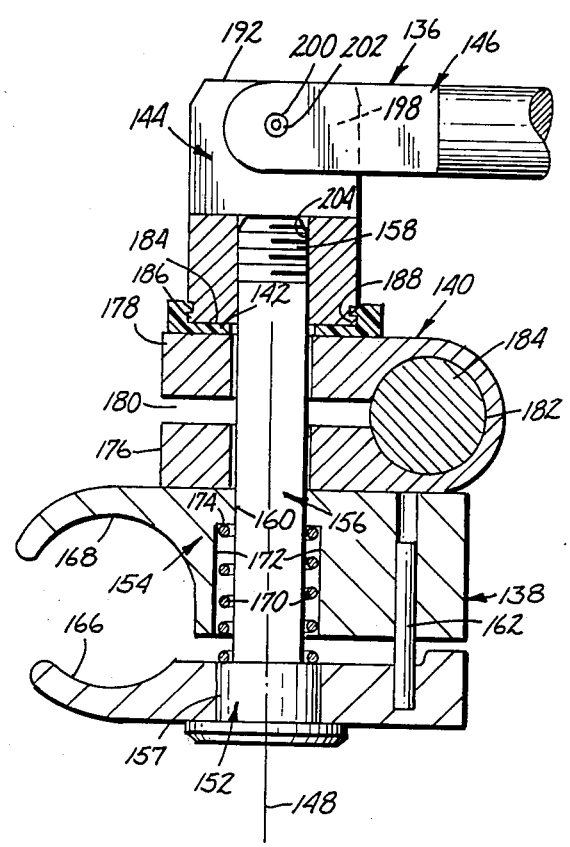
FIG. 5 is a sectional view of the retractor clamping mechanism of FIG. 4 with portions shown whole.

The clamps 118, 120 and 122 are of similar construction and are described collectively with reference to a clamp 136 illustrated in FIGS. 4 and 5. The clamp 136 includes a lower clamping section 138, an upper clamping section 140, a friction-reduction ring 142, a head section 144 and a handle 146. The lower clamping section, the upper clamping section, ring 142 and head section 144 are disposed coaxially about an axis 148. The axis 148 is considered the pivot axis about which the retractor is pivoted, as indicated by arrows 150 in FIG. 1.

The lower clamping section 138, as illustrated in FIGS. 4 and 5, includes a lower clamping jaw 152 and an upper clamping jaw 154. A bolt 156 extends upwardly through an aperture 157 in the lower clamping jaw 152. The bolt 156 has a threaded upper end 158 and is coaxially disposed on the axis 148 and extends through an aperture 160 of the upper clamping jaw 154. A pin 162 fixedly attached to the lower jaw 152 also extends upwardly and through a bore 164 in the upper clamping jaw 154. The pin 162 and bolt 156 cooperate to retain the upper and lower clamping jaws 152 and 154 in clamping alignment with each other.

The lower clamping jaw 152 has a lower clamping groove 166 and the upper clamping jaw has an upper clamping groove 168 facing the lower clamping groove 166. The lower clamping groove 166 and the upper clamping groove 168 are aligned along their longitudinal axis, as best illustrated in FIG. 5, for clamping the retractor support rod 102, as illustrated in FIG. 1.

A coil spring 170 is coaxially disposed about the bolt 156. The coil spring, at a lower end, abuts against an upper surface of the clamping plate 152 and extends into a downwardly facing bore 172 of the upper clamping plate 154. The bore 172 is disposed coaxially with respect to the bore 160 and the axis 148 and forms a downwardly facing shoulder 174 against which the spring 170 abuts at an upper end. The spring 170 provides a force to separate the lower and upper clamping sections 152 and 154 from a clamping position.

The upper clamping section 140 includes a lower clamping leg 176 and an upper clamping leg 178 separated by a slot 180 that extends from an end 181 of the upper clamping section up to a retractor handle clamping groove 182 located proximate an opposite end 183. The upper clamping section 140 is of a unitary construction, preferably machined from a single block of stainless steel. The legs 176 and 178 are resiliently movable with respect to each other such that the clamping bore 182 is reduced sufficiently in size to frictionally clamp a retractor handle 184. The retractor handle 184 represents retractor handles 126, 132 and 134, as illustrated in FIG. 1.

The upper clamping section 140 also includes a bore 186 coaxially disposed about the axis 148 and through which the bolt 156 extends. When a force is applied such that the legs 176 and 178 are pushed towards each other, the clamping groove 182 clamps around the handle 184 of the retractor securing the retractor in a fixed position.

The friction-reduction ring 142 abuts against an upper surface of the upper clamping section 140. The ring 142 includes an annular shoulder 184 whose outer periphery is defined by an annular wall 186. The head section 144 has a lower annular flange portion 188 that engages the annular shoulder 184 of the ring 142 with the wall 186 engaging sides of the flange 188. The head section 144 includes spaced apart upwardly extending handle retaining members 190 and 192 separated by a slot 194, as best illustrated in FIG. 4. A pin receiving bore 196 extends through the retaining member 192 and is in alignment with another pin receiving bore (not shown) extending through retaining member 190.

The handle 146 includes a slot engaging portion 198 that movably engages the slot 194. The slot engaging portion 198 includes a third pin receiving bore 200 that is alignable with the first pin receiving bore 196 and the second pin receiving bore in the member 190 (not shown). A spring pin 202 engages the bore 196, the bore 200 and the bore (not shown) in the member 190 such that the handle 146 pivots about the pin 202 within the slot 194. The handle 146 is pivotable approximately 180° from a substantially horizontal position on one side of the head section 144 to an opposite side of the head section 144 to facilitate the operation of the retractor clamp regardless of the relative position of the handle 146.

The head section 144 includes a downwardly facing bolt engaging threaded bore 204 that is coaxially aligned with the bore 186 of the upper clamping section and the aperture bore of the upper clamping jaw 154 such that the bolt 156 extends through the bore 160, the bore 186 and into the bore 204, threadably engaging said bore 204.

When the head section 144 is turned clockwise by grasping the handle 146, the lower clamping jaw 152 and the upper clamping jaw 154 are moved towards each other against the force of the spring 170 and the clamping legs 176 and 178 of the upper clamping section 140 are also moved towards each other substantially simultaneously clamping a retractor handle positioned within the clamping grooves 166 and 168 and the retractor support rod 184 in the clamping bore 182. To release the retractor from a clamping position within the clamping grooves 166 and 168 and to release the clamp from the retractor support rod 184, the handle is turned in the opposite direction, turning the head 144 with the spring 170 acting to separate the upper and lower clamping jaws 152 and 154 and the legs 176 and 178 separating due to the resilient force within the clamping section 140.

As is easily understood by those skilled in the art from the discussion above, the retractor support apparatus requires very little space. Any obstruction to the surgeon or the other attendants by the support apparatus is minimal. Although the apparatus takes up a minimal amount of space, the support apparatus is a very rigid and durable structure primarily due to the clamping mechanisms 30 and 100. The frusto-conical section and recess provide a retaining force that includes a large area of metal to metal contact. Once the metal to metal contact is established, clamps 30 and 100 cannot be moved from their selected positions by any force normally found in the operating room, such as a surgeon or attendant leaning or bumping against the apparatus. The retractor support rod 102, since it is a rod and not a flat plate, provides minimum obstruction to the surgeon working in the area 19. However, due to the structure of clamps 30 and 100, the retractor support rod 102 is held in a sufficiently rigid fashion that is capable of withstanding contact by the surgeon and other attendants while retaining the position that had been previously selected.

An auxiliary retractor support device 210 is also illustrated in FIG. 1. The auxiliary retractor support device includes a first support rod section 212, a clamping section 214 and a second retractor support rod section 216. The auxiliary retractor support device is secured to the support rod 18 proximate a free end of the first rod section 212 by a clamp 218. The clamp 218 is of a similar structure as the clamp 30 illustrated in FIGS. 2 and 3. The clamp 218 also provides three degrees of freedom for positioning the retractor support device 210 about three separate axes. First, the clamp 218 and the retractor device 210 are pivotable about an axis running through the support rod 18, as indicated by the arrows 28. Second, the clamp 218, like the clamp 30, has a first clamping section 220 and a second clamping section 222 which are pivotable about an axis generally indicated by the arrows 224. The auxiliary retractor support device 210 is pivotable about the axis indicated by arrows 224 when the clamping section 222 is moved with respect to the clamping section 220. Third, the retractor support device is pivotable about the axis of the rod section 212, as indicated by arrows 226 when the rod section 212 is rotated within the clamping bore of the clamping section 222. In addition, the device 210 is movable along the support rod 18 and along the axis of the rod section 212.

The clamping device 210 is more fully illustrated in FIGS. 6 and 7. The clamping device 210 permits pivoting of the rod sections 212 and 216 about an axis 228 running through the clamping section 214. The clamping section 214 includes a lower clamping member 230, a resilient bushing 232 and an upper clamping member 234. The clamping device also includes a friction-reduction ring 236, a turning bolt 238 for bringing the clamping members 230 and 234 in clamping relationship, and a handle 240 for turning the bolt 238.

The rod section 216 is preferably permanently attached to the lower clamping member 230. The lower clamping member 230 includes an upwardly facing threaded bolt receiving bore 242 for receiving the bolt 238 in threaded cooperation. The lower clamping section includes an upwardly extending frusto-conical portion 244 in coaxial alignment with the bore 242. The frusto-conical portion 244 includes a bushing retaining bore 246 in substantially coaxial alignment with the bore 244. The bore 244 has a lower shoulder 248 for supporting the bushing 232. The bushing 232 has a bolt receiving bore 250 disposed coaxially along the axis 228. The bushing 232 is positioned within the bore 246 and rests on the shoulder 248. The bushing 232 has an upper portion 252 that extends above the frusto-conical portion 244. The bushing 232 is made of a resilient material, such as a medical grade rubber that can be sterilized, and provides a force to separate the clamping members 230 and 234 from the clamping position.

The upper clamping member 234 includes a bore 253 and downwardly facing frusto-conical recess 254, both coaxially aligned along the axis 228. The frusto-conical recess has an upper shoulder 256 that defines the upper limit of the recess and engages the top of the bushing 232. The bushing 232 acting against the shoulder 248 and the shoulder 256 provides a force to separate the lower clamping member 230 from the upper clamping member 234.

The turning bolt 238 has a lower threaded section 258 and an upper head section 260. The turning bolt 238 extends through the ring 236, through the bore 253 of the upper clamping member 234, through the bore 250 of the bushing, and into the bore 242 for threaded engagement. The head section 260 of the turning bolt 238 includes a lower annular flange portion 262 that engages the ring 236. The ring 236 is made of a low friction material, such as "DELRIN". The head section 260 includes first and second handle retaining members 264 and 266 separated by a slot 268. A pin retaining bore 270 extends through the member 264 and a second pin retaining bore 272 extends through the member 262, as best illustrated in FIG. 7.

The handle 240 includes a slot engaging portion 274 that movably engages the slot 268 and includes a third pin engaging bore 276 that is aligned with the bores 270 and 272. A spring pin 278 engages the bore 270, 276 and 272 such that the handle is pivotal approximately from a horizontal position on one side of the turn bolt 238 to an opposite side of the turn bolt 238 or approximately 180°.

When the turn bolt 238 is turned by turning the handle 240 in a clockwise direction, the upper and lower clamping members 234 and 230 are forced together by the threaded engagement of the bolt with the bore 242, moving the bolt through the bore 242. The frusto-conical section 244 and frusto-conical recess 254 frictionally engage each other and retain the members 234 and 230 in a clamping position. When the handle 240 is turned in an opposite direction, the force of the resilient bushing 232 separates the members 230 and 234 moving the clamping device 210 from the clamping position.

Referring back to FIG. 1, the clamping device 210 permits movement of the retractor support rod section 216 about the axis of the clamping device as indicated by arrows 280. The device 210 is used as an auxiliary support alone or in combination with the support rod 102. As illustrated in FIG. 1, the device 210 is positioned so that the rod section 216 runs substantially parallel to the leg 110 of the rod 102. The retractor 17 is mounted to the rod section 216 so that it can be used in cooperation with the retractor 15 mounted on the leg 110 of the rod 102.

The retractor 17 includes a clamping section 282 that clamps the retractor onto the rod section 216 by turning handle 284. The clamping section 282 also permits pivoting of the retractor 17, as indicated by arrow 286, about an axis running through the clamping section 282.

The retractor 15 and the retractor 17 are used in combination to hold back different layers of tissue. The retractor 15 retains a first layer of tissue 288. The retractor 17 is spaced from the retractor 15, as indicated by arrows 290 and 292. The use of the auxiliary device 210 provides the additional flexibility in being able to position the retractor 17 independently from the retractor 15. The device 210 provides versatility since the rod section 216 is positionable independently of the leg 110 of the rod 102. It will be understood that a separate support post, similar to the support post 18, can be clamped to the rail 14 on an opposite side of the table 12 so that the rod section 216 can be positioned along the leg 108. Furthermore, the rod section 216 can be positioned with respect to either sections 112 and 114 of the rod 102 so that a retractor clamp thereon can be used in association with the retractor 13.

Although the present invention has been described with reference to preferred embodiments, workers skilled in the art will recognize that changes may be made in form and detail without departing from the spirit and scope of the invention.

What is claimed is:

1. A clamping mechanism for connecting first and second rod sections of a retractor apparatus, the mechanism comprising:

a first clamping section having a unitary body with a first clamping bore extending therethrough proximate one end of the body and a slot running through said body from the clamping bore to an opposite end of the body, separating the body into first and second resilient leg portions that when brought together reduce the diameter of the first clamping bore for frictionally clamping a rod section, the first clamping section further including a frusto-conical section extending from the first leg portion;

a second clamping section having a unitary body with a second clamping bore extending therethrough proximate one end of the body and a slot running through said body from the clamping bore to an opposite end of the body, separating the body into first and second resilient leg portions that when moved together reduce the diameter of the second clamping bore for frictionally clamping a rod section, the second leg portion having a frusto-conical recess for frictional engagement with the frusto-conical section of the first clamping section such that when a force is applied bringing the first and second clamping sections together and the leg portions of the respective clamping sections together, each clamping bore frictionally clamps the respective rod section and the frusto-conical recess and frusto-conical section are placed in frictional engagement so that the first and second clamping sections are placed in a clamped position; and means for providing a force to bring together the leg portions of the respective clamping section and the first and second clamping sections together.

2. The clamping mechanism of claim 1 wherein the first and second clamping sections have first and second pivot bores coaxially aligned with respect to a pivot axis running through the clamping sections and wherein the means for providing a force includes a turning bolt extending through the pivot bores and threadably engaging the second leg portion of the first clamping section to provide a force to bring the leg portions together when the bolt is turned.

3. The clamping mechanism of claim 2 wherein the turning bolt includes a head section having first and second spaced-apart handle retaining members, each handle retaining member having first and second pin receiving apertures positioned along a pin pivot axis and further including a handle having a section positionable between the first and second retaining members and having a third pin receiving aperture alignable with the first and second pin receiving apertures and a pivot pin insertably engaging the first, second and third apertures, such that the handle is pivotal approximately 180°.

4. A retractor clamping apparatus comprising:

a first clamping member with a first clamping groove;

a second clamping member having a second clamping groove facing the first clamping groove such that the first and second clamping grooves define a first clamping bore which frictionally engages a support rod disposed within the clamping bore when the first and second clamping members are brought together in a clamping relationship;

a support rod clamping section having a unitary body with a second clamping bore extending therethrough proximate one end of the body and a slot running through the body from the clamping bore to an opposite end of the body, separating the body into first and second resilient leg portions that when brought together reduce a diameter of the clamping bore for frictionally clamping a support rod;

spring means for providing a force to separate the first and second clamping members from a clamping position; and means for providing a force to bring together the first and second clamping members to a clamping position and to bring together the leg portions of the rod clamping section to a clamping position.

5. The apparatus of claim 4 wherein the support rod clamping section has a pivot bore extending through the leg portions and the first and second clamping member having pivot bores extending therethrough and the means for providing a force includes a turning bolt extending through the pivot bores of the first and second clamping members and the support rod clamping section and a bolt engaging head member having a threaded bore for threadably engaging the bolt such that when the bolt is turned to move through the threaded bore, a force is provided to bring the first and second clamping members and the first and second leg portions of the retractor clamping apparatus together in a clamping position.

6. The apparatus of claim 5 wherein the head member includes first and second spaced-apart handle retaining members, each handle retaining member having first and second pin receiving apertures positioned along a pin pivot axis and further including a handle having a section positionable between the first and second retaining members and having a third pin receiving aperture alignable with the first and second pin receiving apertures and a pivot pin insertably engaging the first, second and third apertures such that the handle is pivotal approximately 180°.

* * * * *